(12) United States Patent
Nakajima et al.

(10) Patent No.: US 7,262,048 B2
(45) Date of Patent: Aug. 28, 2007

(54) BIOCHEMICAL ANALYSIS UNIT

(75) Inventors: Kenji Nakajima, Minami-ashigara (JP); Akifumi Kato, Minami-ashigara (JP)

(73) Assignee: Fujifilm Corporation, Tokyo (JP)

( * ) Notice: Subject to any disclaimer, the term of this patent is extended or adjusted under 35 U.S.C. 154(b) by 0 days.

(21) Appl. No.: 10/800,676

(22) Filed: Mar. 16, 2004

(65) Prior Publication Data
US 2004/0185550 A1   Sep. 23, 2004

(30) Foreign Application Priority Data
Mar. 19, 2003   (JP)   ............... 2003-075038

(51) Int. Cl.
*C12M 1/34*   (2006.01)
(52) U.S. Cl. ............... 435/287.1; 435/287.2; 435/287.3; 435/288.4; 435/288.7; 422/50; 422/68.1; 422/82.05; 436/518
(58) Field of Classification Search ............... 422/50, 422/61, 82.05, 68.1; 435/4, 6, 283.1, 287.1, 435/287.2, 288.7, 287.3, 287.4; 436/501, 436/518, 523, 529, 530
See application file for complete search history.

(56) References Cited

U.S. PATENT DOCUMENTS

| | | | | |
|---|---|---|---|---|
| 5,192,502 | A * | 3/1993 | Attridge et al. | ............... 422/57 |
| 5,856,203 | A * | 1/1999 | Robinson et al. | ........... 436/518 |
| 6,309,608 | B1 * | 10/2001 | Zhou et al. | ............... 422/131 |
| 6,492,119 | B1 | 12/2002 | Ogawa | |
| 6,664,071 | B1 * | 12/2003 | Windhab et al. | ............ 435/7.94 |
| 6,781,143 | B2 * | 8/2004 | Shimizu et al. | ............. 250/583 |
| 2002/0061534 | A1 | 5/2002 | Ogura | |
| 2002/0094533 | A1 * | 7/2002 | Hess et al. | ..................... 435/6 |
| 2002/0177144 | A1 * | 11/2002 | Remacle et al. | ............... 435/6 |
| 2002/0197568 | A1 * | 12/2002 | Neriishi et al. | ............. 430/496 |
| 2003/0143523 | A1 * | 7/2003 | Kato et al. | ..................... 435/4 |

FOREIGN PATENT DOCUMENTS

| | | | |
|---|---|---|---|
| JP | 2001-083164 A1 | 3/2001 | |
| JP | 3298836 B2 | 4/2002 | |
| JP | 2002-355036 A1 | 12/2002 | |

* cited by examiner

*Primary Examiner*—Long V. Le
*Assistant Examiner*—Melanie J. Yu
(74) *Attorney, Agent, or Firm*—Sughrue Mion, PLLC

(57) ABSTRACT

A biochemical analysis unit comprises a base plate, which has holes, and a porous adsorptive material, which is filled in each of the holes and forms each of adsorptive regions. Each of the adsorptive regions is provided with a layer, which has pores having a comparatively small mean pore diameter, and a layer, which has pores having a comparatively large mean pore diameter. In cases where the layers, which constitute each of the adsorptive regions, are connected with the layers, which constitute an adjacent adsorptive region, at one of surfaces of the base plate, the biochemical analysis unit further comprises a signal absorbing layer for absorbing a signal, which passes through layers located under the base plate and thus propagates from a certain hole toward an adjacent hole.

7 Claims, 4 Drawing Sheets

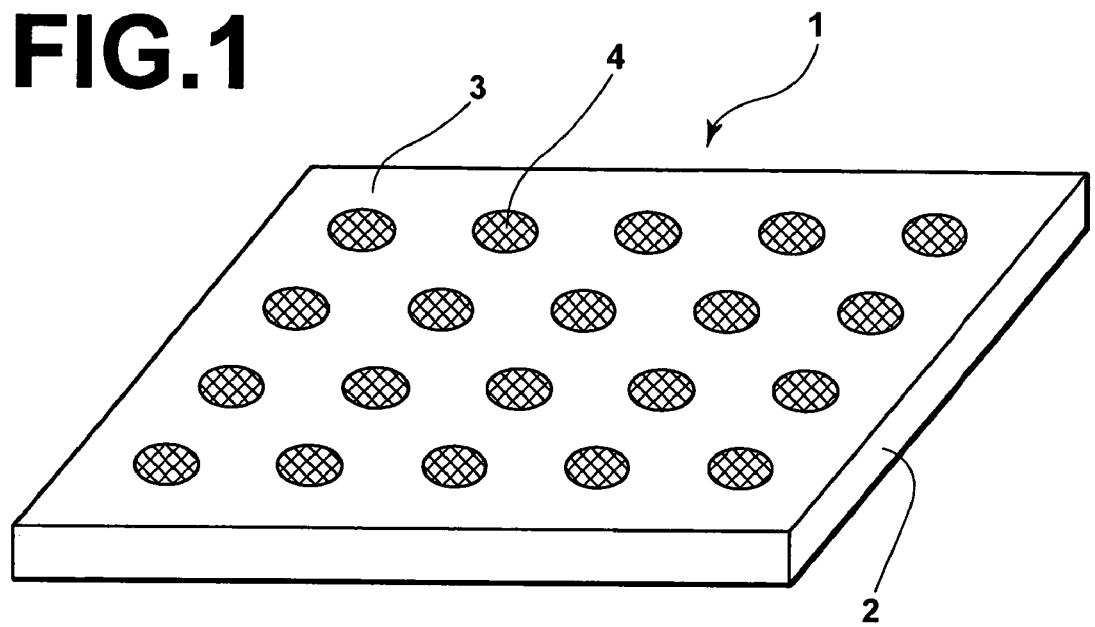
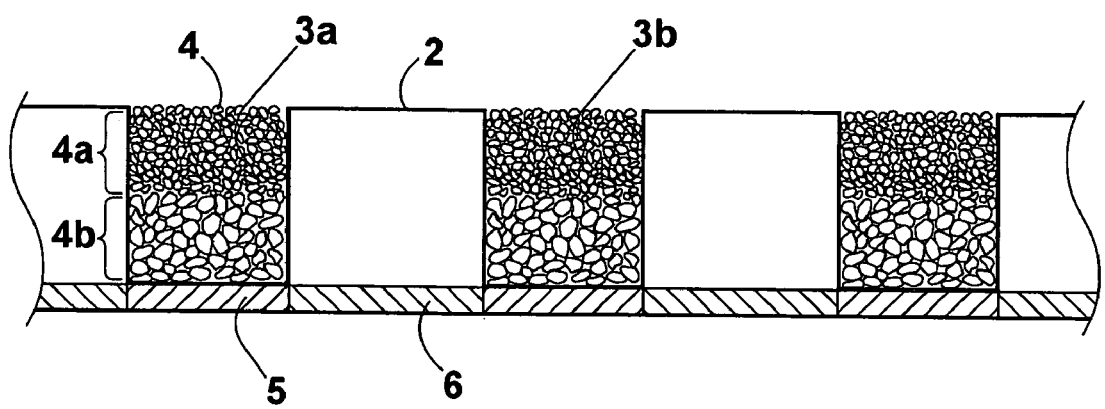

BIOCHEMICAL ANALYSIS UNIT

BACKGROUND OF THE INVENTION

1. Field of the Invention

This invention relates to a biochemical analysis unit for use in an operation for detecting a receptor or a ligand by the utilization of a labeling substance.

2. Description of the Related Art

Heretofore, in the fields of clinical examinations, and the like, analyses of various samples have been made. Also, in order for quick and accurate analyses of the samples to be made, various analysis implements for use in analysis kits and analysis instruments have been proposed. For example, in Japanese Patent No. 3298836, a sample analysis implement comprising an analyzing section and a porous sample introducing section, which has a mean pore diameter larger than the mean pore diameter of the analyzing section, is proposed. The proposed sample analysis implement, wherein the mean pore diameter of the porous sample introducing section is set to be large, and wherein the mean pore diameter of the analyzing section is set to be small, enables the separation of constituents of a sample, such that the sample may be processed quickly.

Also, in the fields of molecular biology, such as genetic expression analysis, macro arrays comprising a membrane and a plurality of spots (dots), which contain biopolymers, such as DNA's, and are arrayed on the membrane, have heretofore been known. With the macro arrays, multiple kinds of samples are capable of being analyzed at one time on a single membrane. Therefore, the macro arrays have heretofore been used widely in the fields of molecular biology and the medical fields. For example, various kinds of DNA fragments (probes) may be arrayed in the form of dots on the macro array, and a target, which has been prepared from mRNA, or the like, may be added onto the macro array. In this manner, hybridization, or the like, may be caused to occur. In such cases, behavior of a plurality of genes can be analyzed at one time.

The conventional macro arrays are constituted of a polymeric organic membrane formed from nitrocellulose, or the like. Therefore, the conventional macro arrays are markedly soft and are apt to suffer from bending and creasing, which adversely affects the analytic operations, and the like. Accordingly, a macro array comprising a film-shaped hard porous body and a plurality of spots, which contain test substances and are arrayed on the film-shaped hard porous body, has been proposed in, for example, U.S. Pat. No. 6,492,119.

Also, various micro array analysis systems and various macro array analysis systems have heretofore been used. With the micro array analysis systems and the macro array analysis systems, liquids containing ligands or receptors (i.e., the substances, which are capable of specifically binding to organism-originating substances and whose base sequences, base lengths, compositions, characteristics, and the like, are known) are spotted onto different positions on a surface of a biochemical analysis unit, such as a membrane filter, and a plurality of adsorptive regions are thereby formed on the surface of the biochemical analysis unit. Examples of the ligands or the receptors include hormones, tumor markers, enzymes, antibodies, antigens, abzymes, other proteins, nucleic acids, cDNA's, DNA's, and RNA's. Thereafter, a labeled receptor or a labeled ligand, which has been labeled with a radioactive labeling substance, a fluorescent labeling substance, a labeling substance capable of causing a chemical luminescence substrate to produce chemical luminescence when being brought into contact with the chemical luminescence substrate, or the like, is subjected to hybridization, or the like, with the ligands or the receptors, which are contained in the adsorptive regions of the biochemical analysis unit. The labeled receptor or the labeled ligand is thus specifically bound to at least one of the ligands or the receptors, which are contained in the adsorptive regions of the biochemical analysis unit. The labeled receptor or the labeled ligand is the substance, which has been sampled from an organism through extraction, isolation, or the like, or has been subjected to chemical treatment after being sampled, and which has been labeled with the radioactive labeling substance, the fluorescent labeling substance, the labeling substance capable of causing a chemical luminescence substrate to produce the chemical luminescence when being brought into contact with the chemical luminescence substrate, or the like. Examples of the labeled receptors or the labeled ligands include hormones, tumor markers, enzymes, antibodies, antigens, abzymes, other proteins, nucleic acids, DNA's, and mRNA's.

In cases where the labeled receptor or the labeled ligand has been labeled with the radioactive labeling substance, a stimulable phosphor layer of a stimulable phosphor sheet is then exposed to radiation radiated out from the radioactive labeling substance, which is contained selectively in the adsorptive regions of the biochemical analysis unit. Thereafter, the stimulable phosphor layer is exposed to stimulating rays, which cause the stimulable phosphor layer to emit light in proportion to the amount of energy stored on the stimulable phosphor layer during the exposure of the stimulable phosphor layer to the radiation. The light emitted by the stimulable phosphor layer is detected photoelectrically, and data for a biochemical analysis is thereby obtained.

In cases where the labeled receptor or the labeled ligand has been labeled with the fluorescent labeling substance, excitation light is irradiated to the adsorptive regions of the biochemical analysis unit, and the fluorescent labeling substance, which is contained selectively in the adsorptive regions of the biochemical analysis unit, is excited by the excitation light to produce fluorescence. The thus produced fluorescence is detected photoelectrically, and data for a biochemical analysis is thereby obtained.

In cases where the labeled receptor or the labeled ligand has been labeled with the labeling substance capable of causing a chemical luminescence substrate to produce the chemical luminescence when being brought into contact with the chemical luminescence substrate, the labeling substance, which is contained selectively in the adsorptive regions of the biochemical analysis unit, is brought into contact with the chemical luminescence substrate. Also, the chemical luminescence produced by the labeling substance is detected photoelectrically, and data for a biochemical analysis is thereby obtained.

The micro array analysis systems and the macro array analysis systems are described in, for example, U.S. Patent Laid-Open No. 20020061534.

With the micro array analysis systems and the macro array analysis systems described above, a large number of the adsorptive regions, to which the ligands or the receptors are bound, are capable of being formed at a high density at different positions on the surface of the biochemical analysis unit, and the labeled receptor or the labeled ligand, which has been labeled with the labeling substance, is capable of being subjected to the hybridization, or the like, with the ligands or the receptors, which have been bound to the adsorptive regions formed at a high density at different positions on the surface of the biochemical analysis unit.

Therefore, the micro array analysis systems and the macro array analysis systems described above have the advantages in that a receptor or a ligand is capable of being analyzed quickly.

[Patent Literature 1]Japanese Patent No. 3298836
[Patent Literature 2]U.S. Pat. No. 6,492,119
[Patent Literature 3]U.S. Patent Laid-Open No. 20020061534

However, the ligand or the receptor, which is bound to each of the adsorptive regions of the biochemical analysis unit described above, is bound and fixed to the entire area of each of the adsorptive regions. Therefore, the problems occur in that a signal coming from the receptor or the ligand having been bound to the ligand or the receptor having been fixed to an area of each of the adsorptive regions, which area is remote from a detection surface, is attenuated. As for the micro array analysis systems and the macro array analysis systems described above, it is desired that the receptor or the ligand be capable of being analyzed more accurately. However, the attenuation of the signal described above obstructs the formation of accurate data for a biochemical analysis.

SUMMARY OF THE INVENTION

The primary object of the present invention is to provide a biochemical analysis unit, which enables attenuation of a signal coming from a receptor or a ligand to be suppressed.

In Patent Literature 2 described above, it is described that the film-shaped hard porous body is constituted of a surface layer region, which is provided with through-pores having a comparatively small mean pore diameter, and a base layer region, which is provided with through-pores having a comparatively large mean pore diameter. However, the film-shaped hard porous body described in Patent Literature 2 should be distinctly distinguished from a biochemical analysis unit in accordance with the present invention comprising a base plate, which has a plurality of holes, and a porous adsorptive material, which is filled in each of the plurality of the holes of the base plate. Further, the constitution described in Patent Literature 2, wherein the film-shaped hard porous body is constituted of the surface layer region, which is provided with the through-pores having a comparatively small mean pore diameter, and the base layer region, which is provided with the through-pores having a comparatively large mean pore diameter, is the constitution which aims at the effect such that a liquid containing a probe may quickly penetrate into the film-shaped hard porous body when the liquid containing the probe is spotted onto the film-shaped hard porous body. The constitution of the film-shaped hard porous body aiming at the effect described above is clearly different from the constitution of the biochemical analysis unit in accordance with the present invention.

The present invention provides a first biochemical analysis unit, comprising:

i) a base plate, which has a plurality of holes, and ii) a porous adsorptive material, which is filled in each of the plurality of the holes of the base plate and forms each of a plurality of adsorptive regions, wherein each of the adsorptive regions is provided with a layer, which has pores having a comparatively small mean pore diameter, and a layer, which has pores having a comparatively large mean pore diameter.

The term "pore diameter" as used herein means the mean value of the values of the longest diameter and the shortest diameter of a certain hole. The difference in mean pore diameter between the layer, which has the pores having a comparatively small mean pore diameter, and the layer, which has the pores having a comparatively large mean pore diameter, may vary in accordance with the layer thickness of the layer, which has the pores having a comparatively small mean pore diameter, the layer thickness of the layer, which has the pores having a comparatively large mean pore diameter, or the like. However, in cases where the mean pore diameter of the pores of the layer, which has the pores having a comparatively large mean pore diameter, is taken as 1, the mean pore diameter of the pores of the layer, which has the pores having a comparatively small mean pore diameter, should preferably be at most 0.7, should more preferably be at most 0.5, and should most preferably be at most 0.4.

The first biochemical analysis unit in accordance with the present invention should preferably be modified such that the layers, which constitute each of the adsorptive regions, are connected with the layers, which constitute an adjacent adsorptive region, at one of surfaces of the base plate, and the biochemical analysis unit further comprises a signal absorbing layer for absorbing a signal, which passes through layers located under the base plate and thus propagates from a certain hole of the base plate toward an adjacent hole of the base plate.

The present invention also provides a second biochemical analysis unit, comprising:

i) a base plate, which has a plurality of holes, and ii) a porous adsorptive material, which is filled in each of the plurality of the holes of the base plate and forms each of a plurality of adsorptive regions, wherein each of the adsorptive regions is provided with a layer constituted of a material having a comparatively large quantity of a functional group, which is capable of binding with a ligand or a receptor to be bound to the adsorptive region, and a layer constituted of a material having a comparatively small quantity of a functional group, which is capable of binding with the ligand or the receptor to be bound to the adsorptive region.

The kind of the functional group, which is capable of binding with the ligand or the receptor to be bound to the adsorptive region, may vary in accordance with the kind of the ligand or the receptor, which is to be bound to the adsorptive region. Examples of the functional groups include a carboxyl group, an amino group, an amido group which becomes capable of binding with the ligand or the receptor when being exposed to ultraviolet light, a group for forming an ester linkage which becomes capable of binding with the ligand or the receptor when being subjected to saponification treatment, and a hydroxyl group which becomes capable of binding with the ligand or the receptor by the aid of a silane coupling agent.

The difference between the quantity of the functional group, which is contained in the layer constituted of the material having a comparatively large quantity of the functional group, and the quantity of the functional group, which is contained in the layer constituted of the material having a comparatively small quantity of the functional group, may vary in accordance with the layer thickness of the layer constituted of the material having a comparatively large quantity of the functional group, the layer thickness of the layer constituted of the material having a comparatively small quantity of the functional group, the kind of the functional group, or the like. However, in cases where the density of the functional group in the layer constituted of the material having a comparatively large quantity of the functional group is taken as 1, the density of the functional group in the layer constituted of the material having a comparatively small quantity of the functional group should preferably be at most 0.7, should more preferably be at most 0.5, and should most preferably be at most 0.4.

The second biochemical analysis unit in accordance with the present invention should preferably be modified such that the layers, which constitute each of the adsorptive regions, are connected with the layers, which constitute an adjacent adsorptive region, at one of surfaces of the base plate, and the biochemical analysis unit further comprises a signal absorbing layer for absorbing a signal, which passes through layers located under the base plate and thus propagates from a certain hole of the base plate toward an adjacent hole of the base plate.

The first biochemical analysis unit in accordance with the present invention comprises the base plate, which has the plurality of the holes, and the porous adsorptive material, which is filled in each of the plurality of the holes of the base plate and forms each of the plurality of the adsorptive regions. Also, each of the adsorptive regions is provided with the layer, which has the pores having a comparatively small mean pore diameter, and the layer, which has the pores having a comparatively large mean pore diameter. Therefore, with the first biochemical analysis unit in accordance with the present invention, the layer, which has the pores having a comparatively small mean pore diameter, has a large specific surface area and is capable of efficiently immobilizing the ligand or the receptor. Also, the layer, which has the pores having a comparatively large mean pore diameter, is capable of uniformly distributing a reaction liquid over the entire area of the biochemical analysis unit and enhancing the self-supporting characteristics of the porous adsorptive material. Specifically, a part of the functions of the adsorptive region is capable of being assigned to the layer, which has the pores having a comparatively small mean pore diameter, and the other part of the functions of the adsorptive region is capable of being assigned to the layer, which has the pores having a comparatively large mean pore diameter.

The ligand or the receptor, which is to be immobilized, converges upon the layer, which has the pores having a comparatively small mean pore diameter. Therefore, in cases where a receptor or a ligand, which has been specifically bound to the immobilized ligand or the immobilized receptor, is to be detected by the utilization of a signal coming from a labeling substance, the detection of the receptor or the ligand may be performed from the side of the layer, which has the pores having a comparatively small mean pore diameter. In such cases, the detection of the receptor or the ligand is capable of being performed such that the signal coming from the receptor or the ligand may not be attenuated.

The second biochemical analysis unit in accordance with the present invention comprises the base plate, which has the plurality of the holes, and the porous adsorptive material, which is filled in each of the plurality of the holes of the base plate and forms each of the plurality of the adsorptive regions. Also, each of the adsorptive regions is provided with the layer constituted of the material having a comparatively large quantity of the functional group, which is capable of binding with a ligand or a receptor to be bound to the adsorptive region, and the layer constituted of the material having a comparatively small quantity of the functional group, which is capable of binding with the ligand or the receptor to be bound to the adsorptive region. Therefore, with the second biochemical analysis unit in accordance with the present invention, the layer constituted of the material having a comparatively large quantity of the functional group is capable of efficiently immobilizing the ligand or the receptor. Also, the layer constituted of the material having a comparatively small quantity of the functional group is capable of uniformly distributing the reaction liquid over the entire area of the biochemical analysis unit and enhancing the self-supporting characteristics of the porous adsorptive material. Further, the layer constituted of the material having a comparatively small quantity of the functional group is capable of preventing the problems from occurring in that the receptor or the ligand undergoes non-specific adsorption by an electrostatic interaction or a polar interaction. Specifically, a part of the functions of the adsorptive region is capable of being assigned to the layer constituted of the material having a comparatively large quantity of the functional group, and the other part of the functions of the adsorptive region is capable of being assigned to the layer constituted of the material having a comparatively small quantity of the functional group.

The ligand or the receptor, which is to be immobilized, converges upon the layer constituted of the material having a comparatively large quantity of the functional group. Therefore, in cases where the receptor or the ligand, which has been specifically bound to the immobilized ligand or the immobilized receptor, is to be detected by the utilization of the signal coming from the labeling substance, the detection of the receptor or the ligand may be performed from the side of the layer constituted of the material having a comparatively large quantity of the functional group. In such cases, the detection of the receptor or the ligand is capable of being performed such that the signal coming from the receptor or the ligand may not be attenuated.

Each of the first biochemical analysis unit and the second biochemical analysis unit in accordance with the present invention may be modified such that the layers, which constitute each of the adsorptive regions, are connected with the layers, which constitute an adjacent adsorptive region, at one of surfaces of the base plate, and such that the biochemical analysis unit further comprises the signal absorbing layer for absorbing the signal, which passes through the layer located under the base plate and thus propagates from a certain hole of the base plate toward an adjacent hole of the base plate. With each of the modification of the first biochemical analysis unit in accordance with the present invention and the modification of the second biochemical analysis unit in accordance with the present invention, the problems are capable of being efficiently prevented from occurring in that the signal coming from the receptor or the ligand, which is to be detected from a certain hole of the base plate, passes through the layers, which constitute each of the adsorptive regions and are connected with the layers constituting an adjacent adsorptive region at the position under the base plate, and the signal thus propagates toward an adjacent hole of the base plate. Accordingly, only the signal, which comes from the receptor or the ligand that is to be detected, is capable of being detected, and the signal coming from each of the holes of the base plate is capable of being detected accurately.

BRIEF DESCRIPTION OF THE DRAWINGS

FIG. 1 is a schematic perspective view showing an embodiment of the biochemical analysis unit in accordance with the present invention, FIG. 2 is a schematic sectional view showing a part of the embodiment of the biochemical analysis unit in accordance with the present invention.

DESCRIPTION OF THE PREFERRED EMBODIMENTS

Figure 3A:
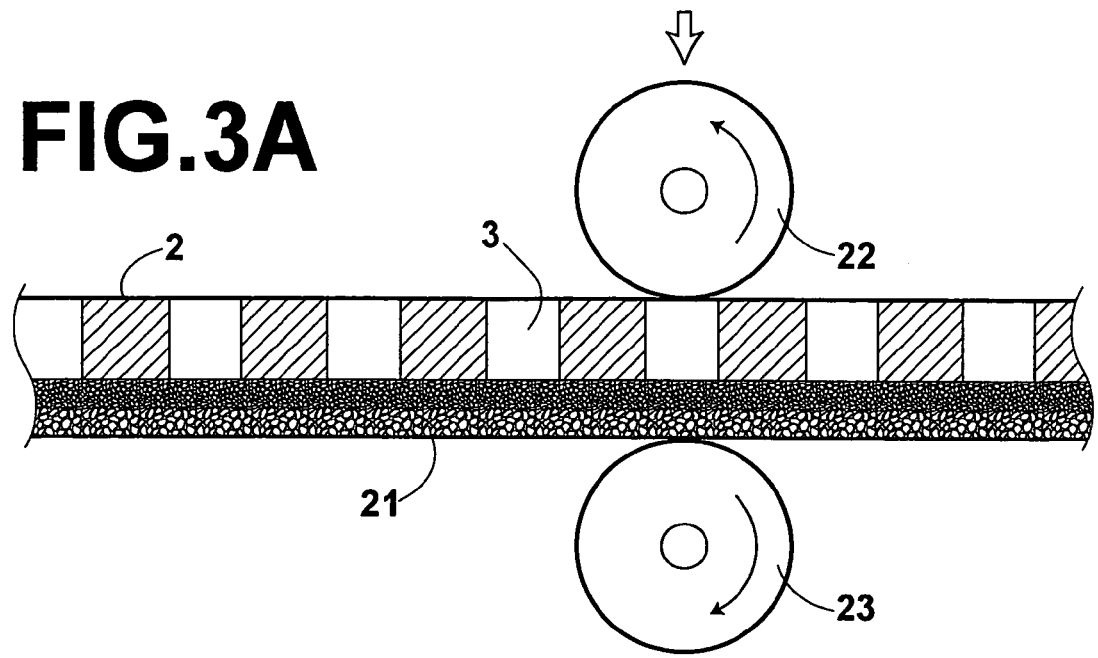
FIGS. 3A and 3B are schematic views showing an example of how the biochemical analysis unit in accordance with the present invention is produced.

The present invention will hereinbelow be described in further detail with reference to the accompanying drawings.

FIG. 1 is a schematic perspective view showing an embodiment of the biochemical analysis unit in accordance with the present invention. With reference to FIG. 1, a biochemical analysis unit 1 comprises a base plate 2, which is provided with a plurality of holes 3, 3, . . . , and a plurality of adsorptive regions 4, 4, . . . , each of which is filled in one of the holes 3, 3, . . . and comprises a porous material adhered to the base plate 2.

FIG. 2 is a schematic sectional view showing a part of the embodiment of the biochemical analysis unit in accordance with the present invention. As illustrated in FIG. 2, each of the adsorptive regions 4, 4, . . . is constituted of a layer 4a, which has pores having a comparatively small mean pore diameter, and a layer 4b, which has pores having a comparatively large mean pore diameter. Also, a signal absorbing layer 5 is formed under the layer 4b, which has the pores having a comparatively large mean pore diameter. The signal absorbing layer 5 absorbs a signal, which passes through an underside area 6 located under the base plate 2 and thus propagates from a hole 3a of the base plate 2 toward an adjacent hole 3b of the base plate 2. At the underside area 6 located under the base plate 2, the layer 4a and the layer 4b, which constitute each of the adsorptive regions 4, 4, . . . , are connected with the layer 4a and the layer 4b, which constitute an adjacent adsorptive region 4. Specifically, the under side area 6 located under the base plate 2 is constituted of the layer 4a, the layer 4b, and the signal absorbing layer 5, which have been compressed by being pressed together against the bottom surface of the base plate 2.

A ligand or a receptor, which is to be fixed to each of the adsorptive regions 4, 4, . . . , converges upon the layer 4a, which has the pores having a comparatively small mean pore diameter, and is scarcely bound to the layer 4b, which has the pores having a comparatively large mean pore diameter. With the biochemical analysis unit 1, the ligand or the receptor, which is fixed to each of the adsorptive regions 4, 4, . . . , converges upon the layer 4a, which has the pores having a comparatively small mean pore diameter. Therefore, in cases where a receptor or a ligand, which has been specifically bound to the ligand or the receptor having been fixed to each of the adsorptive regions 4, 4, . . . , is to be detected by the utilization of a labeling substance, the detection of the receptor or the ligand may be performed from the side of the layer 4a, which has the pores having a comparatively small mean pore diameter. In such cases, the detection of the receptor or the ligand is capable of being performed such that the signal coming from the receptor or the ligand may not be attenuated.

Also, with the biochemical analysis unit 1, at the underside area 6 located under the base plate 2, the layer 4a and the layer 4b, which constitute each of the adsorptive regions 4, 4, . . . , are connected with the layer 4a and the layer 4b, which constitute an adjacent adsorptive region 4. Therefore, there is possibility of the signal propagating from the hole 3a toward the adjacent hole 3b. However, with the biochemical analysis unit 1, wherein the ligand or the receptor, which is to be fixed to each of the adsorptive regions 4, 4, . . . , converges upon the layer 4a, which has the pores having a comparatively small mean pore diameter, the amount of the signal propagating from the hole 3a toward the adjacent hole 3b is capable of being kept smaller than with a biochemical analysis unit, wherein the ligand or the receptor is bound in a dispersed form over the entire area of the adsorptive region. Further, since the biochemical analysis unit 1 is provided with the signal absorbing layer 5, the signal propagating from the hole 3a toward the adjacent hole 3b is capable of being efficiently absorbed by the signal absorbing layer 5. Accordingly, the effect of the signal propagating from the hole 3a toward the adjacent hole 3b is capable of being suppressed.

In FIG. 2, each of the adsorptive regions 4, 4, . . . is constituted of the two layers, i.e. the layer 4a, which has the pores having a comparatively small mean pore diameter, and the layer 4b, which has the pores having a comparatively large mean pore diameter. However, the number of the layers constituting each of the adsorptive regions 4, 4, . . . is not limited to two. For example, the biochemical analysis unit 1 in accordance with the present invention may be modified such that each of the adsorptive regions 4, 4, . . . is constituted of the layer 4a, which has the pores having a comparatively small mean pore diameter, the layer 4b, which has the pores having a comparatively large mean pore diameter, and an intermediate layer, which is formed between the layer 4a and the layer 4b and has pores having a mean pore diameter falling between the comparatively small mean pore diameter of the pores of the layer 4a and the comparatively large mean pore diameter of the pores of the layer 4b.

Also, in FIG. 2, the signal absorbing layer 5 is formed over the entire area of the bottom surface of the base plate 2. Alternatively, the signal absorbing layer 5 may be formed between the layer 4a and the layer 4b. As another alternative, the signal absorbing layer 5 may be formed only at the position exactly under the layer 4b so as to close each of the holes 3, 3, . . . As a further alternative, the signal absorbing layer 5 may be formed only at the position of the underside area 6, at which the layer 4a, the layer 4b, and the signal absorbing layer 5 have been compressed together, such that the signal absorbing layer 5 is capable of absorbing the signal propagating from a certain hole to an adjacent hole. As a still further alternative, the signal absorbing layer 5 may be formed only at a certain part of the underside area 6, at which the layer 4a, the layer 4b, and the signal absorbing layer 5 have been compressed together, such that the signal absorbing layer 5 is capable of absorbing the signal propagating from a certain hole to an adjacent hole.

Such that light scattering may be prevented from occurring within the biochemical analysis unit 1, the base plate 2 should preferably be made from a material, which does not transmit radiation or light, or which attenuates radiation or light. The material for the formation of the base plate 2 should preferably be a metal or a ceramic material. Also, in cases where a plastic material, for which the hole making processing is capable of being performed easily, is employed as the material for the formation of the base plate 2, particles should preferably be dispersed within the plastic material, such that radiation or light is capable of being attenuated even further.

Examples of the metals, which may be utilized preferably for the formation of the base plate 2, include copper, silver, gold, zinc, lead, aluminum, titanium, tin, chromium, iron, nickel, cobalt, tantalum, and alloys, such as stainless steel and bronze. Examples of the ceramic materials, which may be utilized preferably for the formation of the base plate 2, include alumina, zirconia, magnesia, and quartz. Examples of the plastic materials, which may be utilized preferably for the formation of the base plate 2, include polyolefins, such as a polyethylene and a polypropylene; polystyrenes; acrylic resins, such as a polymethyl methacrylate; polyvinyl chlorides; polyvinylidene chlorides; polyvinylidene fluorides; polytetrafluoroethylenes; polychlorotrifluoroethylenes; polycarbonates; polyesters, such as a polyethylene naphthalate and a polyethylene terephthalate; aliphatic polyamides, such as a 6-nylon and a 6,6-nylon; polyimides; polysulfones; polyphenylene sulfides; silicon resins, such as a polydiphenyl siloxane; phenolic resins, such as novolak; epoxy resins; polyurethanes; celluloses, such as cellulose acetate and nitrocellulose; copolymers, such as a butadiene-styrene copolymer; and blends of plastic materials.

Also, in cases where the receptor or the ligand, which is to be detected, is subjected to the specific binding with the ligands or the receptors, each of which has been bound to one of the adsorptive regions 4, 4, . . . , and the receptor or the ligand, which has thus been bound to at least one of the ligands or the receptors having been bound to the adsorptive regions 4, 4, . . . , is to be detected by the utilization of the labeling substance, it is desired that the radiation or the light radiated out from the labeling substance within a hole 3 of the base plate 2 be prevented from passing from the hole 3 through the base plate wall to the adjacent hole 3. Therefore, in cases where the base plate 2 is constituted of a plastic material, in order for the radiation or the light to be attenuated, the plastic material should preferably be loaded with particles of metal oxides, glass fibers, or the like. Examples of the metal oxides include silicon dioxide, alumina, titanium dioxide, iron oxide, and copper oxide. However, the metal oxides are not limited to those enumerated above.

The radiation attenuating properties or the light attenuating properties should preferably be such that, when the radiation or the light, which is radiated out from the labeling substance within the hole 3, has passed from the hole 3 through the base plate wall to the adjacent hole 3, the intensity of the radiation or the light reduces to an intensity of at most $\frac{1}{5}$ of the original intensity. The radiation attenuating properties or the light attenuating properties should more preferably be such that the intensity of the radiation or the light having passed through the base plate wall in the manner described above reduces to an intensity of at most $\frac{1}{10}$ of the original intensity.

In order for the radiation, such as electron rays, coming from a radioactive labeling substance to be blocked efficiently, the mean density of the base plate 2 may ordinarily be at least 0.6 g/cm$^3$. The mean density of the base plate 2 should preferably fall within the range of 1 g/cm$^3$ to 20 g/cm$^3$, and should more preferably fall within the range of 2 g/cm$^3$ to 10 g/cm$^3$. Since the transmission distance of the electron rays is in inverse proportion to the density, in cases where the radioactive labeling substance is an ordinary radioactive isotope (RI), such as $^{32}$P, $^{33}$P, $^{35}$S, or $^{14}$C, and the mean density of the base plate 2 falls within the range described above, the electron rays coming from the RI of the sample, which is fixed within each of the holes 3, 3, . . . , is capable of being blocked by the partition wall of the base plate 2, and the problems are capable of being prevented from occurring in that resolution of a radiation image is adversely affected by transmission and scattering of the electron rays.

The thickness of the base plate 2 may ordinarily fall within the range of 50 μm to 1,000 μm, and should preferably fall within the range of 100 μm to 500 μm.

Such that the density of the holes 3, 3, . . . made through the base plate 2 may be enhanced, the area (size) of the opening of each of the holes 3, 3, . . . may ordinarily be smaller than 5 mm$^2$. The area of the opening of each of the holes 3, 3, . . . should preferably be smaller than 1 mm$^2$, should more preferably be smaller than 0.3 mm$^2$, and should most preferably be smaller than 0.01 mm$^2$. Also, the area of the opening of each of the holes 3 3, . . . should preferably be at least 0.001 mm$^2$.

The pitch of the holes 3, 3, . . . (i.e., the distance between the center points of two holes which are adjacent to each other) should preferably fall within the range of 0.05 mm to 3 mm. Also, the spacing between two adjacent holes 3, 3 (i.e., the shortest distance between edges of two adjacent holes 3, 3) should preferably fall within the range of 0.01 mm to 1.5 mm. The number (the array density) of the holes 3, 3, . . . may ordinarily be at least 10 holes/cm$^2$. The number (the array density) of the holes 3, 3, . . . should preferably be at least 100 holes/cm$^2$, should more preferably be at least 500 holes/cm$^2$, and should most preferably be at least 1,000 holes/cm$^2$. Also, the number (the array density) of the holes 3, 3, . . . should preferably be at most 100,000 holes/cm$^2$, and should more preferably be at most 10,000 holes/cm$^2$. The holes 3, 3, . . . need not necessarily be arrayed at equal spacing as illustrated in FIG. 1. For example, the holes 3, 3, . . . may be grouped into several number of blocks (units) comprising a plurality of holes and may be formed in units of the blocks.

Perforation of the plurality of the holes 3, 3, . . . through the base plate 2 may be performed with, for example, a punching technique for punching with a pin, a technique for electrical discharge machining, in which a pulsed high voltage is applied across electrodes in order to volatilize the base plate material, an etching technique, or a laser beam irradiation technique. In cases where the material of the base plate is a metal material or a plastic material, the biochemical analysis unit may be prepared with an operation for performing corona discharge or plasma discharge on the surface of the base plate, applying an adhesive agent to the surface of the base plate, and laminating the porous material for the formation of the adsorptive regions by use of means, such as a press. The adhesive agent described above should preferably be styrene-butadiene rubber, acrylonitrile-butadiene rubber, or the like. The application of the adhesive agent should preferably be performed with a roll coating technique, a wire bar coating technique, a dip coating technique, a blade coating technique, or the like. Also, in cases where the porous material for the formation of the adsorptive regions is pressed against the base plate, the base plate and the porous material for the formation of the adsorptive regions may be divided previously into a plurality of sheets, and the plurality of the sheets may be pressed intermittently. Alternatively, a long web of the base plate and a long web of the porous material for the formation of the adsorptive regions may be conveyed continuously between two rolls.

In the biochemical analysis unit in accordance with the present invention, as the porous material for the formation of the adsorptive regions of the biochemical analysis unit, a porous quality material or a fiber material may be utilized preferably. The porous quality material and the fiber material may be utilized in combination in order to form the adsorptive regions of the biochemical analysis unit. In the biochemical analysis unit in accordance with the present invention, the porous material, which may be utilized for the formation of the adsorptive regions of the biochemical analysis unit, may be an organic material, an inorganic material, or an organic-inorganic composite material.

The organic porous quality material, which may be utilized for the formation of the adsorptive regions of the biochemical analysis unit, may be selected from a wide variety of materials. However, the organic porous quality material should preferably be a carbon porous quality material, such as active carbon, or a porous quality material capable of forming a membrane filter. As the porous quality material capable of forming a membrane filter, a polymer soluble in a solvent should preferably be utilized. Examples of the polymers soluble in a solvent include cellulose derivatives, such as nitrocellulose, regenerated cellulose, cellulose acetate, and cellulose acetate butyrate; aliphatic polyamides, such as a 6-nylon, a 6,6-nylon, and a 4,10-nylon; polyolefins, such as a polyethylene and a polypropylene; chlorine-containing polymers, such as a polyvinyl chloride and a polyvinylidene chloride; fluorine resins, such as a polyvinylidene fluoride and a polytetrafluoride; polycarbonates; polysulfones; alginic acids and alginic acid derivatives, such as alginic acid, calcium alginate, and an alginic acid-polylysine polyion complex; and collagen. Copolymers or composite materials (mixture materials) of the above-enumerated polymers may also be utilized.

The fiber material, which may be utilized for the formation of the adsorptive regions of the biochemical analysis unit, may be selected from a wide variety of materials. Examples of the fiber materials, which may be utilized preferably, include the cellulose derivatives and the aliphatic polyamides enumerated above.

The inorganic porous quality material, which may be utilized for the formation of the adsorptive regions of the biochemical analysis unit, may be selected from a wide variety of materials. Examples of the inorganic porous quality materials, which may be utilized preferably, include metals, such as platinum, gold, iron, silver, nickel, and aluminum; oxides of metals, and the like, such as alumina, silica, titania, and zeolite; metal salts, such as hydroxyapatite and calcium sulfate; and composite materials of the above-enumerated materials.

After the porous adsorptive material for the formation of the adsorptive regions of the biochemical analysis unit has been selected appropriately, the layer, which has the pores having a comparatively small mean pore diameter, and the layer, which has the pores having a comparatively large mean pore diameter, are formed. Alternatively, a layer constituted of a material having a comparatively large quantity of a functional group, which is capable of binding with a ligand or a receptor to be bound to the adsorptive region, and a layer constituted of a material having a comparatively small quantity of a functional group, which is capable of binding with the ligand or the receptor to be bound to the adsorptive region, may be formed.

Also, the signal absorbing layer is capable of being formed with a process, wherein a substance capable of absorbing the signal, such as a light signal or a radiation signal, is mixed with the porous adsorptive material described above. In cases where the signal is a chemical luminescence signal or a fluorescence signal, the signal absorbing layer is capable of being formed with a process, wherein a dye, or the like, capable of absorbing light having wavelengths falling within the wavelength range of the chemical luminescence or the fluorescence is mixed with the porous adsorptive material described above. In cases where the signal is the radiation signal, the signal absorbing layer is capable of being formed with a process, wherein fine particles of a heavy metal, such as lead or tungsten, which acts as a radiation blocking substance, are mixed with the porous adsorptive material described above.

In order for each of the adsorptive regions to be formed from the layer, which has the pores having a comparatively small mean pore diameter, and the layer, which has the pores having a comparatively large mean pore diameter, the layers may be formed with a process described below. Also, in order for each of the adsorptive regions to be formed from the layer constituted of the material having a comparatively large quantity of the functional group, which is capable of binding with the ligand or the receptor to be bound to the adsorptive region, and the layer constituted of the material having a comparatively small quantity of the functional group, which is capable of binding with the ligand or the receptor to be bound to the adsorptive region, the layers may be formed with a process described below. Specifically, solutions (hereinbelow referred to as the dopes) containing different kinds of porous quality materials in solvents are successively cast or coated on a support, and the resulting casting layers or the resulting coating layers are then dipped in bad solvents for the polymers of the porous films or in a mixed solvent of good solvents and bad solvents for the polymers and thereafter subjected to washing with water and drying. Alternatively, the formation of the layers for forming each of the adsorptive regions may be formed with a different process, wherein one of different kinds of dopes is cast or coated on a support, the other dope is cast or coated on a different support, and each of the resulting casting layers or each of the resulting coating layers is then dried little by little.

Figure 3B:
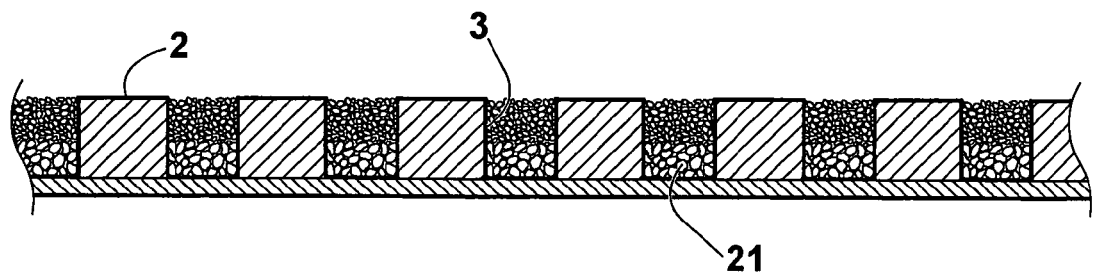

FIGS. 3A and 3B are schematic views showing an example of how the biochemical analysis unit in accordance with the present invention is produced. In the example shown in FIGS. 3A and 3B, the biochemical analysis unit is produced with a pressing technique, wherein a porous film 21, which comprises two layers having pores having different mean pore diameters, and the base plate 2 are superposed one upon the other and pressed together, and the porous film 21 is thereby press-fitted into the holes 3, 3, . . . of the base plate 2. With the pressing technique, the porous film 21 is capable of being press-fitted into the holes 3, 3, . . . of the base plate 2 such that little change occurs with the pore diameters of the pores of the region of the porous film 21, which region is press-fitted into each of the holes 3, 3, . . .

As illustrated in FIG. 3A, the porous film 21 and the base plate 2 having the holes 3, 3, . . . are superposed one upon the other and pressed together by being passed between a press roll 22 and a back-up roll 23. In this manner, as illustrated in FIG. 3B, the porous film 21 is press-fitted into the holes 3, 3, . . . of the base plate 2. In such cases, the porous film 21 may be softened with a technique wherein, for example, the press roll 22 and the back-up roll 23 are heated.

Figure 4:
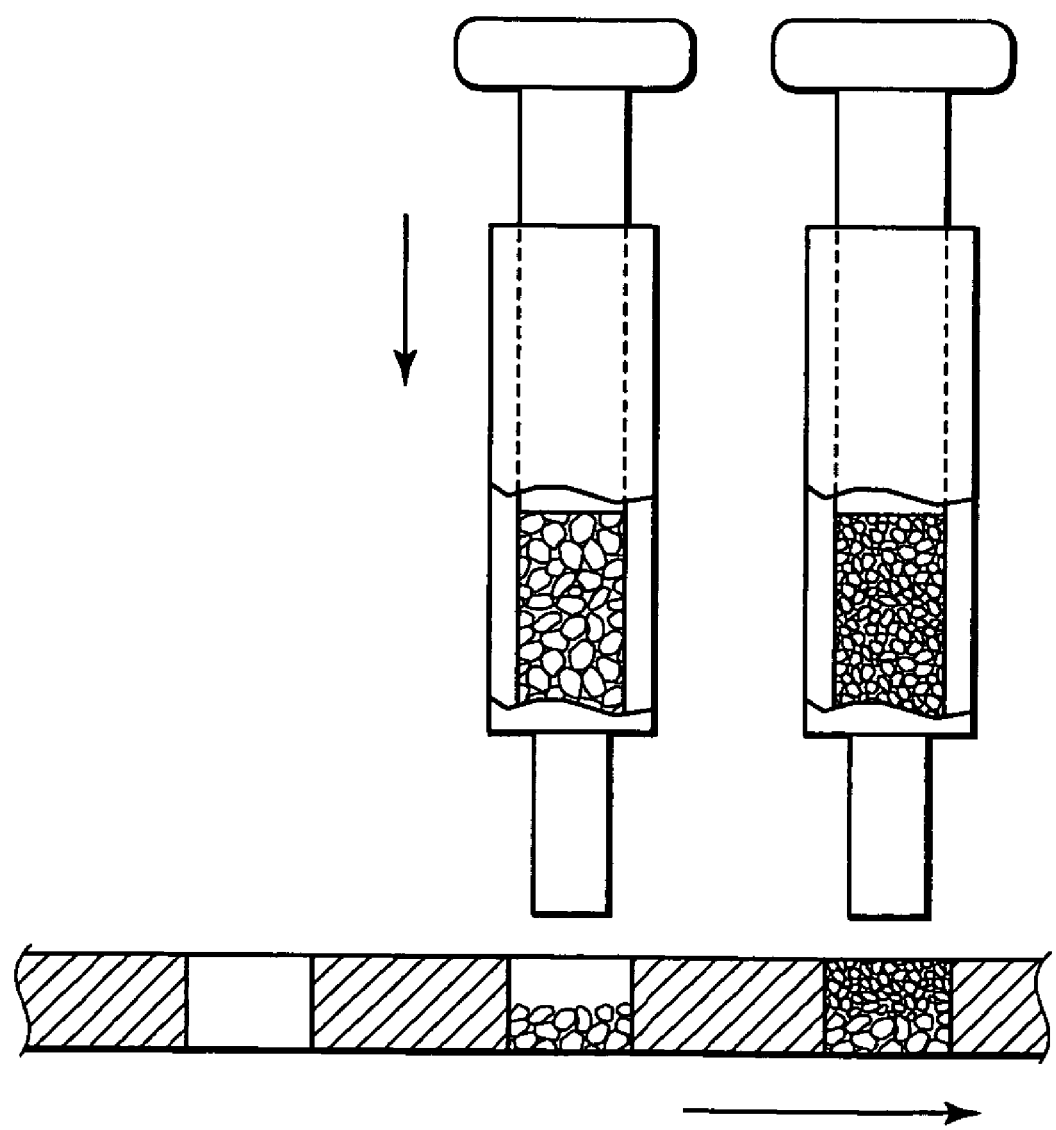
FIG. 4 is a schematic view showing a different example of how the biochemical analysis unit in accordance with the present invention is produced.

Alternatively, the biochemical analysis unit in accordance with the present invention may be produced with a technique, wherein the dopes are injected into the holes 3, 3, . . . of the base plate 2. FIG. 4 is a schematic view showing a different example of how the biochemical analysis unit in accordance with the present invention is produced. As illustrated in FIG. 4, a dispenser 30 for injecting a dope 31 into the holes 3, 3, . . . of the base plate 2 and a dispenser 32 for injecting a dope 33 into the holes 3, 3, . . . of the base plate 2 are located above the base plate 2, which is conveyed continuously or intermittently. In FIG. 4, as an aid in clarifying the relationship between each of the dopes 31 and 33 and the formation of the corresponding layer, the contents of each of the dopes 31 and 33 are shown by the illustration identical with the illustration of the corresponding layer. The dispenser 30 intermittently injects the dope 31 into each of the holes 3, 3, . . . of the base plate 2. Thereafter, the dispenser 32 intermittently injects the dope 33 onto the dope 31 having been injected into each of the holes 3, 3, . . . of the base plate 2. After the dopes 31 and 33 have been injected into each of the holes 3, 3, . . . of the base plate 2, air having a controlled temperature and a controlled humidity is fed over the base plate 2 at a predetermined flow rate, and the solvents contained in the dopes 31 and 33 are vaporized little by little. In this manner, the two different kinds of the layers are capable of being formed.

The biochemical analysis unit in accordance with the present invention is applicable broadly to various assay processes for:

i) obtaining a biochemical analysis unit provided with a plurality of porous adsorptive regions, to which ligands or receptors have been bound respectively, ii) subjecting a reaction liquid containing at least one kind of a receptor or at least one kind of a ligand to specific binding with the ligands or the receptors, each of which has been bound to one of the porous adsorptive regions of the biochemical analysis unit, the receptor or the ligand being thereby specifically bound to at least one of the ligands, each of which has been bound to one of the porous adsorptive regions of the biochemical analysis unit, or at least one of the receptors, each of which has been bound to one of the porous adsorptive regions of the biochemical analysis unit, and iii) detecting the receptor or the ligand,which has thus been specifically bound to at least one of the ligands or at least one of the receptors, by the utilization of a labeling substance.

In a first aspect, the biochemical analysis unit in accordance with the present invention is applicable to an assay process for:

i) obtaining a biochemical analysis unit provided with a plurality of porous adsorptive regions, to which ligands or receptors have been bound respectively, ii) subjecting a reaction liquid containing at least one kind of a labeled receptor or at least one kind of a labeled ligand, which has been labeled with a labeling substance, to specific binding with the ligands or the receptors, each of which has been bound to one of the porous adsorptive regions of the biochemical analysis unit, the labeled receptor or the labeled ligand being thereby specifically bound to at least one of the ligands, each of which has been bound to one of the porous adsorptive regions of the biochemical analysis unit, or at least one of the receptors, each of which has been bound to one of the porous adsorptive regions of the biochemical analysis unit, and iii) detecting the labeled receptor or the labeled ligand, which has thus been specifically bound to at least one of the ligands or at least one of the receptors.

In such cases, the labeled receptor or the labeled ligand is the substance, which has been sampled from an organism through extraction, isolation, or the like, or has been subjected to chemical treatment after being sampled, and which has been labeled with the labeling substance. The labeled receptor or the labeled ligand is capable of undergoing the specific binding with at least one of the ligands, each of which has been bound to one of the porous adsorptive regions of the biochemical analysis unit, or at least one of the receptors, each of which has been bound to one of the porous adsorptive regions of the biochemical analysis unit. Examples of the labeled receptors or the labeled ligands include hormones, tumor markers, enzymes, antibodies, antigens, abzymes, other proteins, nucleic acids, DNA's, and mRNA's.

Examples of the labeling substances include a radioactive labeling substance, a fluorescent labeling substance, and a labeling substance capable of causing a chemical luminescence substrate to produce the chemical luminescence when being brought into contact with the chemical luminescence substrate. The labeling substance maybe a substance, which is capable of producing radiation by itself, a substance, which is capable of emitting light by itself, a substance, which is capable of forming a color by itself, or a substance, which is capable of producing fluorescence by itself when being exposed to light. Alternatively, the labeling substance may be a substance, which is capable of causing a chemical substance to emit light, to form a color, or to produce the fluorescence through, for example, decomposition or reaction of the chemical substance when being brought into contact with the chemical substance. As for the former type of the labeling substance, a radioactive isotope may be employed as the radiation producing labeling substance. Also, an acridinium ester, or the like, may be employed as the light emitting labeling substance. Further, gold colloidal particles, or the like, may be employed as the color forming labeling substance. Furthermore, fluorescein, or the like, may be employed as the fluorescent labeling substance. As the latter type of the labeling substance, an enzyme may be employed. Examples of the enzymes include alkaline phosphatase, peroxidase, luciferase, and β-galactosidase. When one of the above-enumerated enzymes acting as the labeling substance is brought into contact with a chemical luminescence substrate, a dye substrate, or a fluorescence substrate, the enzyme is capable of causing the chemical luminescence substrate to produce the chemical luminescence, causing the dye substrate to form a color, or causing the fluorescence substrate to produce the fluorescence.

By way of example, in cases where the enzyme is alkaline phosphatase, peroxidase, or luciferase, the chemical luminescence substrate may be dioxetane, luminol, or luciferin, respectively. In cases where the enzyme is alkaline phosphatase, the dye substrate may be p-nitrophenyl phosphate. In cases where the enzyme is β-galactosidase, the dye substrate may be p-nitrophenyl-β-D-galactoside, or the like. In cases where the enzyme is alkaline phosphatase, the fluorescence substrate may be 4-methylumbelliferphosphoric acid. In cases where the enzyme is peroxidase, the fluorescence substrate may be 3-(4-hydroxyphenyl)-propionic acid. In cases where the enzyme is β-galactosidase, the fluorescence substrate may be 4-methylumbellifer-β-D-galactoside, or the like.

In a second aspect, the biochemical analysis unit in accordance with the present invention is applicable to an assay process for:

i) obtaining a biochemical analysis unit provided with a plurality of porous adsorptive regions, to which ligands or receptors have been bound respectively, ii) subjecting a reaction liquid containing at least one kind of a receptor or at least one kind of a ligand to specific binding with the ligands or the receptors, each of which has been bound to one of the porous adsorptive regions of the biochemical analysis unit, the receptor or the ligand being thereby specifically bound to at least one of the ligands, each of which has been bound to one of the porous adsorptive regions of the biochemical analysis unit, or at least one of the receptors, each of which has been bound to one of the porous adsorptive regions of the biochemical analysis unit, iii) subjecting a labeled body, which has been labeled with a labeling substance, to specific binding with the receptor or the ligand having been specifically bound to at least one of the ligands, each of which has been bound to one of the porous adsorptive regions of the biochemical analysis unit, or at least one of the receptors, each of which has been bound to one of the porous adsorptive regions of the biochemical analysis unit, and iv) detecting the receptor or the ligand, which has been specifically bound to at least one of the ligands or at least one of the receptors.

The aforesaid second aspect of the assay process is the so-called sandwich technique, wherein the receptor or the ligand, which is to be detected, is sandwiched between the ligand or the receptor, which has been bound to the adsorptive region, and the labeled body. In this case, the receptor or the ligand, which is to be detected, is the substance, which has been sampled from an organism through extraction, isolation, or the like, or has been subjected to chemical treatment after being sampled, and which has been labeled with the labeling substance. The receptor or the ligand is capable of undergoing the specific binding with at least one of the ligands, each of which has been bound to one of the porous adsorptive regions of the biochemical analysis unit, or at least one of the receptors, each of which has been bound to one of the porous adsorptive regions of the biochemical analysis unit. Examples of the receptors or the ligands, which are to be detected, include hormones, tumor markers, enzymes, antibodies, antigens, abzymes, other proteins, nucleic acids, DNA's, and mRNA's.

The labeled body, which has been labeled with the labeling substance, is a body, which has been labeled with the labeling substance described above and is capable of undergoing the specific binding with a reaction site of the receptor or the ligand, which is to be detected. Examples of the labeled bodies include antigens, antibodies, hormones, tumor markers, enzymes, abzymes, other proteins, nucleic acids, cDNA's, DNA's, and RNA's, whose characteristics, compositions, structures, base sequences, base lengths, and the like, are known.

In a third aspect, the biochemical analysis unit in accordance with the present invention is applicable to an assay process for:

i) obtaining a biochemical analysis unit provided with a plurality of porous adsorptive regions, to which ligands or receptors have been bound respectively, ii) subjecting a reaction liquid containing at least one kind of an auxiliary substance-bound receptor or at least one kind of an auxiliary substance-bound ligand, to which an auxiliary substance has been bound, to specific binding with the ligands or the receptors, each of which has been bound to one of the porous adsorptive regions of the biochemical analysis unit, the auxiliary substance-bound receptor or the auxiliary substance-bound ligand being thereby specifically bound to at least one of the ligands, each of which has been bound to one of the porous adsorptive regions of the biochemical analysis unit, or at least one of the receptors, each of which has been bound to one of the porous adsorptive regions of the biochemical analysis unit, iii) subjecting an auxiliary substance-combinable labeling substance, which is capable of undergoing specific binding with the auxiliary substance, to specific binding with the auxiliary substance-bound receptor or the auxiliary substance-bound ligand having been specifically bound to at least one of the ligands, each of which has been bound to one of the porous adsorptive regions of the biochemical analysis unit, or at least one of the receptors, each of which has been bound to one of the porous adsorptive regions of the biochemical analysis unit, and iv) detecting the auxiliary substance-bound receptor or the auxiliary substance-bound ligand, which has been specifically bound to at least one of the ligands or at least one of the receptors.

The auxiliary substance is a substance capable of undergoing the binding with the auxiliary substance-combinable labeling substance. Examples of preferable auxiliary substances include antigens, such as digoxigenin, biotin, avidin, and fluorescein, and antibodies with respect to the above-enumerated antigens. Also, the auxiliary substance may be a biological binding partner, such as avidin with respect to biotin. In this case, the auxiliary substance-combinable labeling substance is a substance, which is capable of undergoing the specific binding with the auxiliary substance and has been labeled with the labeling substance described above.

How a biochemical analysis using the biochemical analysis unit in accordance with the present invention is performed will be described hereinbelow by taking a chemical luminescence technique as an example.

In the chemical luminescence technique using the biochemical analysis unit in accordance with the present invention, firstly, the ligands or the receptors are bound respectively to the adsorptive regions of the biochemical analysis unit, which is provided with the plurality of the adsorptive regions. In cases where each of the adsorptive regions of the biochemical analysis unit is provided with the layer, which has the pores having a comparatively small mean pore diameter, and the layer, which has the pores having a comparatively large mean pore diameter, the binding of the ligand or the receptor with each of the adsorptive regions is performed from the side of the layer, which has the pores having a comparatively small mean pore diameter. Also, in cases where each of the adsorptive regions of the biochemical analysis unit is provided with the layer constituted of the material having a comparatively large quantity of the functional group, which is capable of binding with the ligand or the receptor to be bound to the adsorptive region, and the layer constituted of the material having a comparatively small quantity of the functional group, which is capable of binding with the ligand or the receptor to be bound to the adsorptive region, the binding of the ligand or the receptor with each of the adsorptive regions is performed from the side of the layer constituted of the material having a comparatively large quantity of the functional group, which is capable of binding with the ligand or the receptor to be bound to the adsorptive region. After the ligands or the receptors have been spotted respectively onto the adsorptive regions of the biochemical analysis unit, the ligands or the receptors are capable of being fixed to the adsorptive regions with ultraviolet light irradiation, or the like.

As described above, the binding of the ligand or the receptor with each of the adsorptive regions is performed from the side of the layer, which has the pores having a comparatively small mean pore diameter. Also, the binding of the ligand or the receptor with each of the adsorptive regions is performed from the side of the layer constituted of the material having a comparatively large quantity of the functional group, which is capable of binding with the ligand or the receptor to be bound to the adsorptive region. As a result, the ligand or the receptor, which is fixed to each of the adsorptive regions, converges upon the layer, which has the pores having a comparatively small mean pore diameter.

Also, the ligand or the receptor, which is fixed to each of the adsorptive regions, converges upon the layer constituted of the material having a comparatively large quantity of the functional group, which is capable of binding with the ligand or the receptor to be bound to the adsorptive region.

Thereafter, a labeled receptor or a labeled ligand, which has been labeled with a labeling substance, is subjected to specific binding with the ligands or the receptors, each of which has been bound to one of the adsorptive regions of the biochemical analysis unit. In order to perform the specific binding of labeled receptor or the labeled ligand with the ligands or the receptors, each of which has been bound to one of the adsorptive regions of the biochemical analysis unit, a reactor, in which a reaction liquid is capable of being forcibly caused to flow such that the reaction liquid flows across each of the adsorptive regions of the biochemical analysis unit, is utilized.

Figure 5:
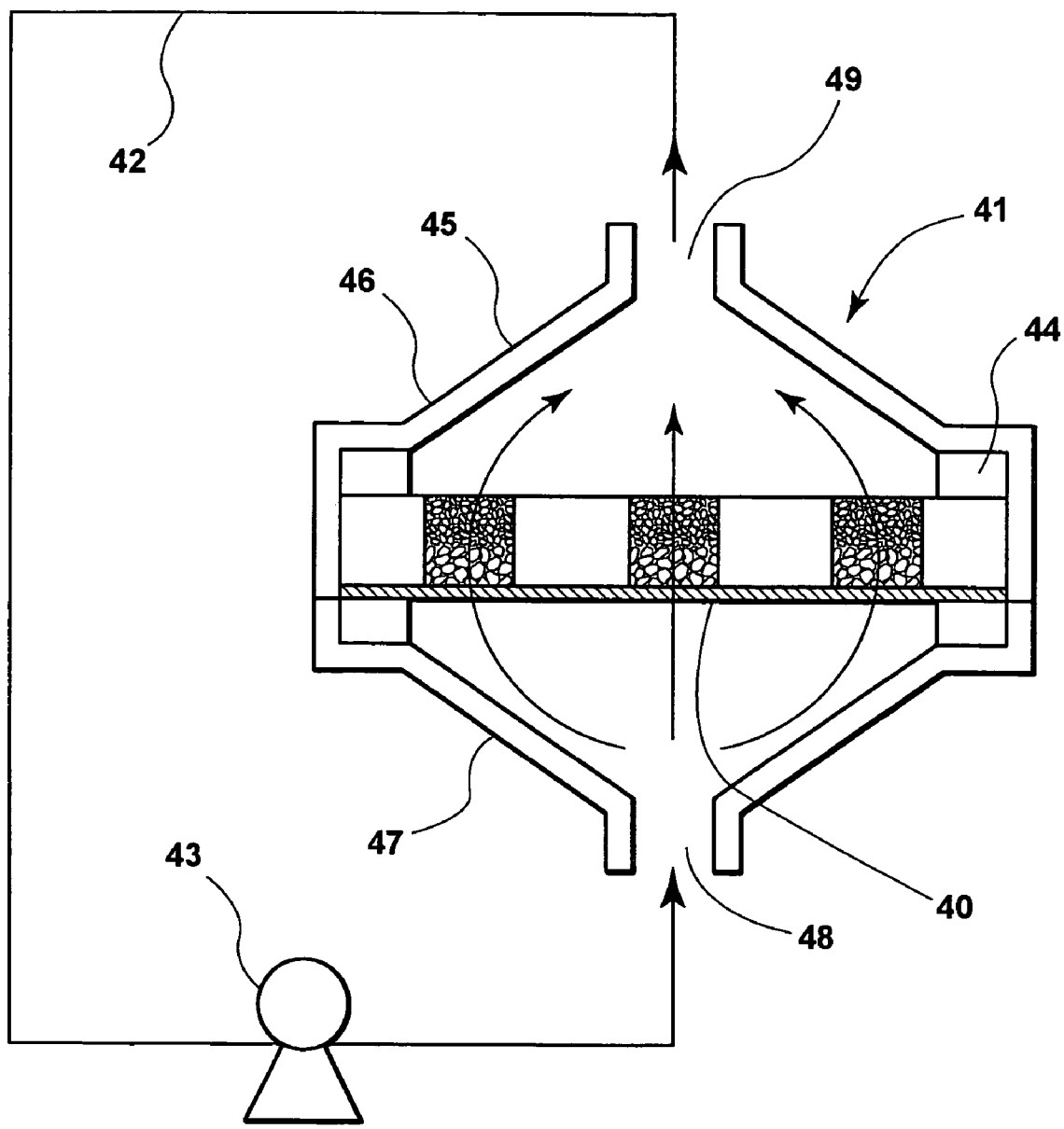
FIG. 5 is a schematic sectional view showing an example of a reactor, in which a reaction liquid is forcibly caused to flow.

FIG. 5 is a schematic sectional view showing an example of a reactor, in which a reaction liquid is capable of being forcibly caused to flow. With reference to FIG. 5, the reactor comprises a reaction vessel 41, a liquid circulating pipe 42 and a pump 43. The reaction vessel 41 is provided with a biochemical analysis unit support section 44, which supports a biochemical analysis unit 40 and has sealing functions for preventing liquid leakage. A reaction vessel main body 45 of the reaction vessel 41 comprises a reaction vessel upper half 46 and a reaction vessel lower half 47. The reaction vessel upper half 46 is releasably secured to the reaction vessel main body 45. When the biochemical analysis unit 40 is to be set within the reaction vessel 41, the reaction vessel upper half 46 is dismounted from the reaction vessel main body 45, and the biochemical analysis unit 40 is set within the reaction vessel 41. A bottom wall of the reaction vessel lower half 47 is provided with a liquid inlet 48, through which a liquid is capable of flowing. Also, a top wall of the reaction vessel upper half 46 is provided with a liquid outlet 49, through which the liquid is capable of flowing. Further, the liquid circulating pipe 42 is releasably fitted to the liquid inlet 48 and the liquid outlet 49 of the reaction vessel 41. The reactor is constituted such that the liquid is introduced by the pump 43 into the reaction vessel main body 45 through the liquid inlet 48, passed through the biochemical analysis unit 40, discharged through the liquid outlet 49, and circulated through the liquid circulating pipe 42.

The biochemical analysis unit 40 provided with the adsorptive regions, to which the ligands or the receptors have been bound respectively, is set in the reactor. Also, the reaction liquid containing the labeled receptor or the labeled ligand is introduced into the reaction vessel 41. Thereafter, the pump 43 is actuated, and the reaction liquid is forcibly caused to flow such that the reaction liquid flows across each of the adsorptive regions of the biochemical analysis unit 40. In this manner, the labeled receptor or the labeled ligand is capable of being subjected to the specific binding with the ligands or the receptors, which have been bound respectively to the adsorptive regions of the biochemical analysis unit 40. As described above, the ligand or the receptor, which is fixed to each of the adsorptive regions of the biochemical analysis unit 40, converges upon one of the layers constituting each of the adsorptive regions of the biochemical analysis unit 40. The biochemical analysis unit 40 may be set in the reactor such that the layer, upon which the fixed ligand or the fixed receptor converges, stands facing the upstream side of the flow of the reaction liquid, which is forcibly caused to flow. Alternatively, the biochemical analysis unit 40 may be set in the reactor such that the layer other than the layer, upon which the fixed ligand or the fixed receptor converges, stands facing the upstream side of the flow of the reaction liquid, which is forcibly caused to flow.

The reactor illustrated in FIG. 5 is constituted such that the reaction liquid is forcibly caused to flow in one direction by the pump 43. Alternatively, for example, a reactor may be constituted such that a syringe and a piston are utilized in lieu of the pump 43, and the reaction liquid is caused to undergo reciprocal flowing within the reaction vessel. As another alternative, a reactor may be utilized, in which the reaction liquid merely passes through the biochemical analysis unit 40 from below (or from above) and is not circulated.

In the aforesaid example, the specific binding is performed by use of the reactor, which is capable of forcibly causing the reaction liquid to flow such that the reaction liquid flows across each of the adsorptive regions of the biochemical analysis unit. However, the biochemical analysis unit in accordance with the present invention is not limited to the use within the reactor described above. For example, the biochemical analysis unit in accordance with the present invention may be utilized for the shaking technique, wherein the biochemical analysis unit and the reaction liquid are put into a hybridization bag, vibrations are given to the hybridization bag, and the labeled receptor or the labeled ligand is thus moved through convection or diffusion and is specifically bound to one of the ligands or the receptors having been fixed to the adsorptive regions of the biochemical analysis unit.

However, in cases where each of the adsorptive regions of the biochemical analysis unit is provided with the layer, which has the pores having a comparatively small mean pore diameter, and the layer, which has the pores having a comparatively large mean pore diameter, the biochemical analysis unit should preferably be set within the aforesaid reactor, which is capable of forcibly causing the reaction liquid to flow such that the reaction liquid flows across each of the adsorptive regions of the biochemical analysis unit. In such cases, the pressure drag of the reaction liquid within the layer, which has the pores having a comparatively large mean pore diameter, is capable of being kept small, and the flow rate of the reaction liquid is capable of being enhanced. Therefore, an enhanced reaction efficiency is capable of being expected.

The ligand or the receptor, which has been bound to each of the adsorptive regions of the biochemical analysis unit, converges upon one of the layers constituting each of the adsorptive regions of the biochemical analysis unit. Therefore, the labeled receptor or the labeled ligand, which is bound to at least one of the ligands or the receptors having been bound respectively to the adsorptive regions of the biochemical analysis unit, converges upon one of the layers constituting each of the adsorptive regions of the biochemical analysis unit.

In order for the labeled receptor or the labeled ligand, which has not been specifically bound to the ligands or the receptors having been bound respectively to the porous adsorptive regions of the biochemical analysis unit, to be removed, the biochemical analysis unit having been set within the reaction vessel should preferably be washed with a technique for forcibly causing a washing liquid to flow across each of the adsorptive regions. In such cases, since the washing liquid is forcibly caused to flow across each of the adsorptive regions, the labeled receptor or the labeled ligand, which has not been specifically bound to the ligands or the receptors having been bound respectively to the porous adsorptive regions of the biochemical analysis unit, is capable of being peeled off and removed efficiently. Therefore, the washing efficiency is capable of being enhanced markedly.

After a reaction liquid, which contains an enzyme-labeled antibody described later, is forcibly caused to flow such that the reaction liquid flows across each of the adsorptive regions of the biochemical analysis unit, and the enzyme-labeled antibody is thus subjected to the specific binding with the labeled receptor or the labeled ligand, the enzyme-labeled antibody, which has not been specifically bound to the labeled receptor or the labeled ligand, may be removed. In cases where the enzyme-labeled antibody, which has not been specifically bound to the labeled receptor or the labeled ligand, is to be removed, the washing process described above should preferably be performed. In this manner, the enzyme-labeled antibody, which has not been specifically bound to the labeled receptor or the labeled ligand, is capable of being peeled off and removed efficiently. Therefore, the washing efficiency is capable of being enhanced markedly.

Before the enzyme-labeled antibody is subjected to the specific binding with the labeled receptor or the labeled ligand having been specifically bound to at least one of the ligands, each of which has been bound to one of the adsorptive regions of the biochemical analysis unit, or at least one of the receptors, each of which has been bound to one of the adsorptive regions of the biochemical analysis unit, the adsorptive regions should preferably be blocked with a blocking process, wherein a blocking buffer with respect to the enzyme-labeled antibody is forcibly caused to flow such that the blocking buffer flows across each of the adsorptive regions. With the blocking process, the problems are capable of being prevented from occurring in that, instead of the enzyme-labeled antibody being subjected to the specific binding with the antigen of the labeled receptor or the labeled ligand, the enzyme-labeled antibody is directly bound to the adsorptive regions of the biochemical analysis unit.

Thereafter, the reaction liquid, which contains the enzyme-labeled antibody, is forcibly caused to flow such that the reaction liquid flows across each of the adsorptive regions of the biochemical analysis unit, and the enzyme-labeled antibody is thus subjected to the specific binding with the labeled receptor or the labeled ligand. The enzyme-labeled antibody is the antibody with respect to the labeling substance of the labeled receptor or the labeled ligand, which antibody has been labeled with an enzyme. (In cases where the labeling substance of the labeled receptor or the labeled ligand is an antibody, the enzyme-labeled antibody is the antigen with respect to the labeling substance of the labeled receptor or the labeled ligand, which antigen has been labeled with an enzyme.)

After the enzyme-labeled antibody has thus been subjected to the specific binding with the labeled receptor or the labeled ligand, the washing liquid is forcibly caused to flow across each of the adsorptive regions of the biochemical analysis unit, and the enzyme-labeled antibody, which has not been specifically bound to the labeled receptor or the labeled ligand, is thereby removed. Thereafter, a chemical luminescence substrate is fed into the adsorptive regions and thus brought into contact with the enzyme-labeled antibody, which has been specifically bound to the labeled receptor or the labeled ligand.

In cases where the chemical luminescence substrate and the enzyme are brought into contact with each other, the chemical luminescence having wavelengths falling within the visible light wavelength range is produced. Therefore, the produced chemical luminescence may be detected photoelectrically from the side of the biochemical analysis unit, on which side the ligands or the receptors having been bound to the adsorptive regions have converged. The image data for a biochemical analysis may thus be formed in accordance with the detected chemical luminescence. In this manner, the labeled receptor or the labeled ligand is capable of being detected and determined without the signal coming from the labeling substance being attenuated.

The present invention will further be illustrated by the following nonlimitative examples.

EXAMPLES

Example 1

With an etching technique, 2,500 fine holes were formed in a SUS304 sheet (acting as a base plate material sheet) having a size of 50 mm×50 mm and a thickness of 100 µm. Each of the fine holes had a circular opening region having a hole diameter of 0.3 mm. The fine holes were formed at a hole pitch of 0.45 mm.

Thereafter, as filling materials to be filled in adsorptive regions, two kinds of 6,6-nylons having different polymerization degrees (hereinafter referred to as the high-polymerization-degree 6,6-nylon and the low-polymerization-degree 6,6-nylon), which were supplied by Aldrich Co., were prepared. A solution of the high-polymerization-degree 6,6-nylon was prepared by dissolving 10 g of the high-polymerization-degree 6,6-nylon in 52 g of formic acid. Also, a solution of the low-polymerization-degree 6,6-nylon was prepared by dissolving 10 g of the low-polymerization-degree 6,6-nylon in 52 g of formic acid. The thus prepared solution of the high-polymerization-degree 6,6-nylon had a viscosity of 6.25 Pa·s, and the solution of the low-polymerization-degree 6,6-nylon had a viscosity of 0.94 Pa·s. Thereafter, 15 g of deionized water was added per 85 g of the solution of the high-polymerization-degree 6,6-nylon. Also, 15 g of deionized water was added per 85 g of the solution of the low-polymerization-degree 6,6-nylon. Thereafter, the solution of the low-polymerization-degree 6,6-nylon was cast to uniform wet thickness onto a clean glass plate. The solution of the high-polymerization-degree 6,6-nylon was then cast to uniform wet thickness onto the cast layer of the solution of the low-polymerization-degree 6,6-nylon. The wet thickness of the cast layer of the solution of the low-polymerization-degree 6,6-nylon was 300 µm. The wet thickness of the cast layer of the solution of the high-polymerization-degree 6,6-nylon was 100 µm. The total wet thickness of the combination of the cast layer of the solution of the low-polymerization-degree 6,6-nylon and the cast layer of the solution of the high-polymerization-degree 6,6-nylon was thus 400 µm.

Thereafter, the combination of the cast layer of the solution of the low-polymerization-degree 6,6-nylon and the cast layer of the solution of the high-polymerization-degree 6,6-nylon was dipped in an aqueous formic acid solution containing formic acid and deionized water in a formic acid: deionized water ratio of 45:55. In this manner, fine pores were formed in the cast layer of the solution of the low-polymerization-degree 6,6-nylon and the cast layer of the solution of the high-polymerization-degree 6,6-nylon. The combination of the cast layer of the solution of the low-polymerization-degree 6,6-nylon and the cast layer of the solution of the high-polymerization-degree 6,6-nylon, in which the fine pores had been formed, were then dried. Observation of a film cross-section of the combination of the two cast layers revealed that a layer having comparatively large pores (with diameters of approximately 1 μm) was formed from the cast layer of the solution of the low-polymerization-degree 6,6-nylon, and a layer having comparatively small pores (with diameters of approximately 0.4 μm) was formed from the cast layer of the solution of the high-polymerization-degree 6,6-nylon. (The layer having comparatively small pores, which layer had been formed from the cast layer of the solution of the high-polymerization-degree 6,6-nylon, will hereinbelow be referred to as the finer pore layer.) The thickness of the thus obtained film having the multi-layer structure was 180 μm.

Thereafter, an adhesive agent was applied to one surface of the base plate described above, and the adhesive agent, which entered into the holes having been formed in the base plate, was removed by suction. The adhesive agent remaining on the surface of the base plate was then dried. Thereafter, the adsorptive region forming material having the multi-layer structure described above was pressed against the surface of the base plate, which surface had been coated with the adhesive agent. The adsorptive region forming material having the multi-layer structure described above was thus press-fitted into the fine holes of the base plate and laminated with the surface of the base plate, which surface had been coated with the adhesive agent. The press-fitting process was performed with a calendering technique at a pressure of 100 kPa/cm. (The temperature of one of calendering roll was set at 150° C., and the temperature of the other calendering roll was set at 50° C.) In this manner, a biochemical analysis unit was prepared.

Also, 10 nl of a pBR328-DNA liquid having a concentration of 25 ng/μl (supplied by Roche Diagnostics K.K.), in which the pBR328-DNA had been converted into a single stranded form by thermal denaturation, was spotted onto each of the adsorptive regions of the biochemical analysis unit having been prepared in the manner described above. The spotting was performed from the side of the finer pore layer of each of the adsorptive regions of the biochemical analysis unit. Thereafter, with irradiation of ultraviolet light (254 nm, 33 mJ/cm$^2$), the single stranded pBR328-DNA was fixed to the adsorptive regions of the biochemical analysis unit.

Thereafter, 71 g of disodium hydrogen phosphate (anhydrous) was dissolved in 800 ml of deionized water having been sterilized, and the pH value of the resulting solution was adjusted at 7.2 by the addition of 3 ml to 4 ml of phosphoric acid. Also, the total volume was made up to 1,000 ml by the addition of deionized water having been sterilized. In this manner, a 1 M phosphoric acid buffer was prepared. Thereafter, 7 g of a dodecyl sulfonic acid sodium salt was added to 50 ml of the thus prepared phosphoric acid buffer and 43 ml of deionized water having been sterilized. The resulting mixture was heated, and the dodecyl sulfonic acid sodium salt was dissolved with stirring. Also, 200 μl of a 0.5M EDTA was added. In this manner, a hybridization solution was prepared.

Also, a pBR328-DNA liquid (supplied by Roche Diagnostics K.K.), which had been labeled with digoxigenin (DIG) and had a concentration of 5 ng/μl, was diluted with a TE buffer solution (a mixed solution of 10 mM of Tris-HCL and 1 mM of EDTA, supplied by Nippon Gene K.K.). The DIG-labeled pBR328-DNA liquid was then subjected to thermal denaturation, and the DIG-labeled pBR328-DNA was thus converted into a single stranded form. Thereafter, the DIG-labeled pBR328-DNA liquid was diluted with the hybridization solution described above. In this manner, a hybridization reaction liquid, which contained the DIG-labeled pBR328-DNA at a concentration of 10 pg/ml, was prepared.

Thereafter, the biochemical analysis unit described above was put in a hybridization bag, and 10 ml of the hybridization reaction liquid was introduced into the hybridization bag. The biochemical analysis unit was thus subjected to a hybridization reaction at a temperature of 68° C. for 18 hours with a shaking technique. After the hybridization reaction was performed, a washing liquid was fed into the hybridization bag, and the biochemical analysis unit was washed with the washing liquid.

Also, a washing buffer (supplied by Roche Diagnostics K.K.) was diluted with sterilized deionized water to a concentration of 1/10, and a washing liquid for chemical luminescence was thereby prepared. The thus prepared washing liquid for chemical luminescence was introduced into the hybridization bag, in which the biochemical analysis unit had been accommodated, and a shaking operation was performed for five minutes.

Thereafter, by use of a maleic acid buffer (supplied by Roche Diagnostics K.K.), which had been diluted with sterilized deionized water to a concentration of 1/10, a blocking buffer solution (supplied by Roche Diagnostics K.K.) was diluted to a concentration of 1/10. The thus diluted blocking buffer solution was then subjected to filtration with a polyether sulfone filter (pore diameter: 0.2 μm) and then utilized as a blocking agent. The blocking agent was fed into the hybridization bag, from which the washing liquid had been discharged. A shaking operation was then performed for one hour, and a blocking reaction was thus performed.

Thereafter, an anti-digoxigenin-AP-conjugate (an alkaline phosphatase-labeled digoxigenin antibody, supplied by Roche Diagnostics K.K.) was subjected to centrifugal filtration with a polyvinylidene fluoride filter (pore diameter: 0.2 μm). The anti-digoxigenin-AP-conjugate having been collected by filtration was then diluted with the aforesaid blocking agent to a concentration of 0.75 U/ml, and an enzyme-labeled antibody liquid was thereby prepared. Thereafter, 5 ml of the thus prepared enzyme-labeled antibody liquid was fed into the hybridization bag, from which the blocking agent had been discharged. A shaking operation was then performed for one hour, and an antigen-antibody reaction was thus performed.

After the antigen-antibody reaction was completed, the aforesaid washing liquid for chemical luminescence was fed into the hybridization bag, and the biochemical analysis unit was washed with the washing liquid for chemical luminescence. The biochemical analysis unit was taken out from the hybridization bag and was then brought into contact with a liquid containing a chemical luminescence substrate (CDP-star, ready to use, supplied by Roche Diagnostics K.K.). Also, the chemical luminescence, which was emitted from the adsorptive regions of the biochemical analysis unit, was detected photoelectrically by use of a cooled CCD camera (LAS1000, supplied by Fuji Photo Film Co., Ltd.). The photoelectric detection of the chemical luminescence was performed from the side of the finer pore layer of each of the adsorptive regions of the biochemical analysis unit. In this manner, a digital signal was formed.

Example 2

The chemical luminescence operations were performed in the same manner as that in Example 1, except that adsorptive regions of a biochemical analysis unit were formed such that the wet thickness of the cast layer of the solution of the low-polymerization-degree 6,6-nylon was 200 μm, the wet thickness of the cast layer of the solution of the high-polymerization-degree 6,6-nylon was 200 μm, and the total wet thickness of the combination of the cast layer of the solution of the low-polymerization-degree 6,6-nylon and the cast layer of the solution of the high-polymerization-degree 6,6-nylon was thus 400 μm. Also, a digital signal was formed in the same manner as that in Example 1.

Example 3

The chemical luminescence operations were performed in the same manner as that in Example 1, except that adsorptive regions of a biochemical analysis unit were formed such that the wet thickness of the cast layer of the solution of the low-polymerization-degree 6,6-nylon was 100 μm, the wet thickness of the cast layer of the solution of the high-polymerization-degree 6,6-nylon was 300 μm, and the total wet thickness of the combination of the cast layer of the solution of the low-polymerization-degree 6,6-nylon and the cast layer of the solution of the high-polymerization-degree 6,6-nylon was thus 400 μm. Also, a digital signal was formed in the same manner as that in Example 1.

Example 4

A pBR328-DNA liquid, which had been labeled with DIG and had a concentration of 5 ng/μl, was diluted with a TE buffer solution. The DIG-labeled pBR328-DNA liquid was then subjected to thermal denaturation, and the DIG-labeled pBR328-DNA was thus converted into a single stranded form. Thereafter, the DIG-labeled pBR328-DNA liquid was diluted with a hybridization solution, which was prepared in the same manner as that in Example 1. In this manner, a hybridization reaction liquid, which contained the DIG-labeled pBR328-DNA at a concentration of 1 pg/ml, was prepared.

Thereafter, a biochemical analysis unit, which had been prepared in the same manner as that in Example 2, and in which the single stranded pBR328-DNA had been fixed to the adsorptive regions, was set in the reaction vessel of the reactor illustrated in FIG. 5. Also, 4 ml of the hybridization reaction liquid was fed into the reaction vessel, in which the biochemical analysis unit had been accommodated. The pump of the reactor was actuated, and a hybridization reaction was performed at a temperature of 68° C. for 18 hours. After the hybridization reaction was finished, the pump was actuated, and the adsorptive regions of the biochemical analysis unit were washed.

Thereafter, the washing liquid for chemical luminescence, which was prepared in Example 1, was fed into the reaction vessel, in which the biochemical analysis unit had been accommodated. The pump was then actuated for five minutes, and the liquid in the adsorptive regions of the biochemical analysis unit was thus replaced by the washing liquid for chemical luminescence. Thereafter, the washing liquid was discharged from the reaction vessel, and the blocking agent, which had been prepared in Example 1, was fed into the reaction vessel. The pump was then driven for 10 minutes. In this manner, the liquid at all parts of the adsorptive regions of the biochemical analysis unit was replaced by the blocking agent. Thereafter, the operation of the pump was ceased, and the blocking agent was allowed to stand for 50 minutes within the reaction vessel.

Thereafter, the blocking agent was discharged from the reaction vessel, and 5 ml of the enzyme-labeled antibody liquid, which was prepared in Example 1, was fed into the reaction vessel. The pump was then driven for one minute. In this manner, the liquid at all parts of the adsorptive regions of the biochemical analysis unit was replaced by the enzyme-labeled antibody liquid. Thereafter, the operation of the pump was ceased, and the enzyme-labeled antibody liquid was allowed to stand for one hour within the reaction vessel.

After the antigen-antibody reaction was completed, the washing buffer described above was fed into the reaction vessel. Also, the pump was driven, and the biochemical analysis unit was thus washed. Thereafter, the pump was driven, and the chemical luminescence substrate (CDP-star, ready to use, supplied by Roche Diagnostics K.K.) was brought into contact with the adsorptive regions of the biochemical analysis unit. Also, the chemical luminescence, which was emitted from the adsorptive regions of the biochemical analysis unit, was detected photoelectrically by use of the cooled CCD camera (LAS1000, supplied by Fuji Photo Film Co., Ltd.). The photoelectric detection of the chemical luminescence was performed from the side of the finer pore layer of each of the adsorptive regions of the biochemical analysis unit. In this manner, a digital signal was formed.

Comparative Example 1

A solution of the high-polymerization-degree 6,6-nylon, which was employed in Example 1, was prepared in the same manner as that in Example 1. A biochemical analysis unit was then prepared in the same manner as that in Example 1, except that the solution of the high-polymerization-degree 6,6-nylon was uniformly cast onto a clean glass plate, such that the wet thickness of the cast layer of the solution of the high-polymerization-degree 6,6-nylon was 400 μm, and the adsorptive regions were thereby constituted. By use of the thus prepared biochemical analysis unit, the chemical luminescence operations were performed in the same manner as that in Example 1. Also, a digital signal was formed in the same manner as that in Example 1.

Comparative Example 2

A solution of the low-polymerization-degree 6,6-nylon, which was employed in Example 1, was prepared in the same manner as that in Example 1. A biochemical analysis unit was then prepared in the same manner as that in Example 1, except that the solution of the low-polymerization-degree 6,6-nylon was uniformly cast onto a clean glass plate, such that the wet thickness of the cast layer of the solution of the low-polymerization-degree 6,6-nylon was 400 μm, and the adsorptive regions were thereby constituted. By use of the thus prepared biochemical analysis unit, the chemical luminescence operations were performed in the same manner as that in Example 1. Also, a digital signal was formed in the same manner as that in Example 1.

Comparative Example 3

The chemical luminescence operations were performed by use of the reactor illustrated in FIG. 5 and in the same manner as that in Example 4, except that a biochemical analysis unit prepared in the same manner as that in Comparative Example 1 was employed. Also, a digital signal was formed in the same manner as that in Example 4.

With each of the biochemical analysis units formed in Examples 1, 2, 3 and Comparative Examples 1 and 2, the intensity of the signal, the intensity of a background, and the signal-to-noise ratio (S/N ratio) listed in Table 1 below were obtained.

TABLE 1

| | Well thickness of low-polymerization-degree 6,6-nylon (μm) | Well thickness of high-polymerization-degree 6,6-nylon (μm) | Signal | Background | S/N ratio |
|---|---|---|---|---|---|
| Example 1 | 300 | 100 | 547300 | 8600 | 63.6 |
| Example 2 | 200 | 200 | 466800 | 6600 | 70.7 |
| Example 3 | 100 | 300 | 437300 | 6900 | 63.4 |
| Comp. Ex. 1 | None | 400 | 378400 | 11500 | 32.9 |
| Comp. Ex. 2 | 400 | None | 351100 | 23000 | 15.3 |

As clear from Table 1, with each of the biochemical analysis units formed in Examples 1, 2, and 3 in accordance with the present invention, wherein each of the adsorptive regions of the biochemical analysis unit is constituted of the layer, which has the pores having a comparatively small mean pore diameter, and the layer, which has the pores having a comparatively large mean pore diameter, the intensity of the digital signal is higher than the intensity of the digital signal obtained with each of the biochemical analysis units formed in Comparative Examples 1 and 2, wherein each of the adsorptive regions of the biochemical analysis unit is constituted of the layer, which has the pores having a single same mean pore diameter, and the intensity of the background was lower than the intensity of the background obtained with each of the biochemical analysis units formed in Comparative Examples 1 and 2. With each of the biochemical analysis units formed in Examples 1, 2, and 3 in accordance with the present invention, the pBR328-DNA (acting as the ligand or the receptor), which has been fixed to each of the adsorptive regions of the biochemical analysis unit, converges upon the finer pore layer (i.e., the layer, which has the pores having a comparatively small mean pore diameter). Also, the DIG-labeled pBR328-DNA (acting as the receptor or the ligand), which has been bound specifically to the pBR328-DNA having been fixed to each of the adsorptive regions of the biochemical analysis unit, converges upon the finer pore layer. Therefore, the chemical luminescence, which is produced when the alkaline phosphatase-labeled digoxigenin antibody, which has been bound to the DIG-labeled pBR328-DNA, is brought into contact with the chemical luminescence substrate (CDP-star), converges upon the finer pore layer. The thus produced chemical luminescence is detected from the side of the finer pore layer of each of the adsorptive regions of the biochemical analysis unit. Therefore, the receptor or the ligand is capable of being detected without the signal being attenuated.

Also, with each of the biochemical analysis units formed in Examples 1, 2, and 3 in accordance with the present invention, at the underside area located under the base plate, the layers, which constitute each of the adsorptive regions are connected with the layers, which constitute an adjacent adsorptive region. Therefore, there is possibility of the signal propagating from a certain hole toward the adjacent hole. However, with each of the biochemical analysis units formed in Examples 1, 2, and 3 in accordance with the present invention, the pBR328-DNA, which has been fixed to each of the adsorptive regions, converges upon the finer pore layer. Therefore, the amount of the signal propagating from a certain hole toward the adjacent hole is capable of being kept smaller than with each of the biochemical analysis units formed in Comparative Examples 1 and 2, wherein the pBR328-DNA is bound in a dispersed for mover the entire area of the adsorptive region. Accordingly, with each of the biochemical analysis units formed in Examples 1, 2, and 3 in accordance with the present invention, the intensity of the background is capable of being kept low.

With each of the biochemical analysis units formed in Example 4 and Comparative Example 3, the intensity of the signal, the intensity of the background, and the signal-to-noise ratio (S/N ratio) listed in Table 2 below were obtained.

TABLE 2

| | Well thickness of low-polymerization-degree 6,6-nylon (μm) | Well thickness of high-polymerization-degree 6,6-nylon (μm) | Signal | Background | S/N ratio |
|---|---|---|---|---|---|
| Example 4 | 200 | 200 | 259120 | 6320 | 41 |
| Comp. Ex. 3 | None | 400 | 263500 | 10540 | 25 |

In each of Example 4 and Comparative Example 3, the chemical luminescence operations are performed by use of the reactor illustrated in FIG. 5, wherein the reaction liquid is forcibly caused to flow such that the reaction liquid flows across each of the adsorptive regions of the biochemical analysis unit. In such cases, as shown in Table 2, with the biochemical analysis unit formed in Example 4 in accordance with the present invention, wherein each of the adsorptive regions of the biochemical analysis unit is constituted of the layer, which has the pores having a comparatively small mean pore diameter, and the layer, which has the pores having a comparatively large mean pore diameter, the intensity of the digital signal is higher than the intensity of the digital signal obtained with the biochemical analysis unit formed in Comparative Example 3, wherein each of the adsorptive regions of the biochemical analysis unit is constituted of the layer, which has the pores having a single same mean pore diameter, and the intensity of the background was lower than the intensity of the background obtained with the biochemical analysis unit formed in Comparative Example 3.

In each of the biochemical analysis units formed in Examples 1, 2, 3, and 4 in accordance with the present invention, each of the adsorptive regions of the biochemical analysis unit is constituted of the layer, which has the pores having a comparatively small mean pore diameter, and the layer, which has the pores having a comparatively large mean pore diameter. The same effects as those obtained in Examples 1, 2, 3, and 4 in accordance with the present invention are also capable of being obtained in cases where a biochemical analysis unit is employed, wherein each of the adsorptive regions is provided with a layer constituted of a material having a comparatively large quantity of a functional group, which is capable of binding with a ligand or a receptor to be bound to the adsorptive region, and a layer constituted of a material having a comparatively small quantity of a functional group, which is capable of binding with the ligand or the receptor to be bound to the adsorptive region.

What is claimed is:

1. A biochemical analysis unit, comprising:
i) a base plate, which has a plurality of holes, and
ii) a porous adsorptive material, which is filled in each of the plurality of the holes of the base plate and forms each of a plurality of adsorptive regions,
wherein each of the adsorptive regions comprises a first layer and a second layer,
a mean pore diameter of the first layer is larger than a mean pore diameter of the second layer,
wherein the first and the second layer of one of said adsorptive regions is connected with a first and a second layer corresponding to an adjacent one of said adsorptive regions at one of surfaces of the base plate, and
the biochemical analysis unit further comprises a signal absorbing layer for absorbing a signal positioned below the base plate such that the first layer, the second layer and the signal absorbing layer are present below the base plate outside of the adsorptive regions and the signal absorbing layer is present below the first and the second layer in the adsorptive regions.

2. A biochemical analysis unit as defined in claim 1 wherein, a ratio of the mean pore diameter of the second layer to the mean pore diameter of the first layer is at most 0.7.

3. A biochemical analysis unit as defined in claim 1 wherein a ratio of the mean pore diameter of the second layer to the mean pore diameter of the first layer is at most 0.7.

4. A biochemical analysis unit as defined in claim 1 wherein the base plate comprises a material having radiation attenuating properties and/or light attenuating properties.

5. A biochemical analysis unit as defined in claim 1 wherein the base plate comprises a material having radiation attenuating properties and/or light attenuating properties.

6. A biochemical analysis unit as defined in claim 2 wherein the base plate comprises a material having radiation attenuating properties and/or light attenuating properties.

7. A biochemical analysis unit as defined in claim 3 wherein the base plate comprises a material having radiation attenuating properties and/or light attenuating properties.

* * * * *